United States Patent [19]

Sternberg

[11] Patent Number: 5,387,527

[45] Date of Patent: Feb. 7, 1995

[54] USE OF PH DEPENDENCE FOR SCATTER CORRECTION IN FLUORESCENT METHODS

[75] Inventor: James C. Sternberg, Fullerton, Calif.

[73] Assignee: Beckman Instruments, Inc., Fullerton, Calif.

[21] Appl. No.: 905,263

[22] Filed: Jun. 26, 1992

[51] Int. Cl.⁶ ............... G01N 33/542; G01N 33/543
[52] U.S. Cl. .................. 436/518; 436/172; 436/537; 436/800
[58] Field of Search ............ 436/518, 528–535, 436/538, 541, 172, 800, 537, 825; 435/5, 6, 7.1, 968; 549/224, 227

[56] References Cited

U.S. PATENT DOCUMENTS

| | | | |
|---|---|---|---|
| 4,160,016 | 7/1979 | Ullman | 424/8 |
| 4,252,783 | 2/1981 | Kam et al. | 424/8 |
| 4,582,791 | 4/1986 | Khanna et al. | 435/975 X |
| 4,774,339 | 9/1988 | Haughland et al. | 548/405 |
| 4,803,049 | 2/1989 | Hirschfeld et al. | 422/82.07 X |
| 4,822,746 | 4/1989 | Walt | 436/528 |
| 4,945,171 | 7/1990 | Haugland et al. | 546/15 X |
| 5,166,052 | 11/1992 | Cercek et al. | 435/7.24 |

FOREIGN PATENT DOCUMENTS 2090971A 7/1982 United Kingdom .
9201224 1/1992 WIPO ............ 436/172

OTHER PUBLICATIONS

"Fluorescence Polarization Immunoassay II. Analyzer for Rapid, Precise Measurement of Polarization With Use Of Disposable Cuvettes", Chem., 27/7:1198–1201 (1981).

"The Chemist's Ready Reference Handbook", Gershon J. Shugar and John A. Dean, McGraw-Hill Publishing Co., 1990 (Section 7.3: Structural Factors Affecting Photoluminescence).

Sidki et al in Alternative Immunoassays (John Wiley & Sons Ltd.) 1985 pp. 185–191.

Tietz (ed), Textbook of Clinical Chemistry (W. B. Saunders Company) 1986 pp. 83–85 and 410–411.

J. Brashear et al, "Florescence Polarization Immunoassay of Urinary 5-Hydroxy-3-Indoleacetic Acid", *Clin. Chem.*, vol. 35, No. 3, pp. 355–359 (1989).

*Primary Examiner*—David Saunders
*Attorney, Agent, or Firm*—William H. May; P. R. Harder; Janis C. Henry

[57] ABSTRACT

A method for correcting for light scattering affects obtained from a sample to which a fluorophore has been added. In accordance with the invention, a sample to which a fluorophore has been added is irradiated with light in the adsorption band of the fluorophore such that the fluorophore emits light at a different intensity. By manipulating the pH of the sample, and obtaining both pre- and post-manipulation emission light intensity readings, the value of the reading attributed to "light scattering" can be determined, such that correction of an erroneous fluorescence reading can be obtained.

36 Claims, No Drawings

USE OF PH DEPENDENCE FOR SCATTER CORRECTION IN FLUORESCENT METHODS

FIELD OF THE INVENTION

The present invention is generally concerned with fluorescence detection methods as an aid in diagnosis of human and animal health. More particularly, the present invention is directed to methods for measuring the amount of a desired analyte from a sample of bodily fluids based upon a fluorescence value of said sample. In its most specific embodiment, the present invention is a method for correcting for light scattering based upon manipulation of the pH of the sample.

BACKGROUND OF THE INVENTION

Fluorescence is a physical phenomenon based upon the ability of certain molecules to absorb and emit light at different wavelengths. The absorption of light (photons) at a first wavelength is followed by the emission of photons at a second wavelength and different energy state. If the emission is relatively short-lived, i.e., approximately $10^{-8}$ seconds, it is referred to as "fluorescence". "Fluorophores" are substances which release significant amounts of fluorescent light.

The fluorescence of many fluorophores is dependent upon the pH of their environment. Therefore, fluorescence of a particular fluorophore is typically measured in the pH region associated with its maximum intensity. See, for example, U.S. Pat. No. 4,774,339 which is incorporated herein by reference.

Fluorophores can be segregated into two broad classes: "intrinsic fluorescent substances" and "extrinsic fluorescent substances". Intrinsic fluorophores comprise naturally occurring biological molecules whose ability to absorb exciting light and emit fluorescent light is based directly on their internal structure and chemical formulation. Extrinsic fluorophores do not occur naturally; they are developed or created in the laboratory.

In order to be useful in medical diagnostics, e.g., immunoassays, the fluorophore: (1) should be capable of being tightly bound on a chemical entity; (2) should be sensitive to those changes in the environmental test conditions or systems indicative of chemical change; and (3) should only minimally affect the features or properties of the molecule being investigated. Investigators typically utilize one of two approaches to bind the fluorophore to a ligand or the analyte of interest: (1) direct binding; or (2) chemically combining the fluorophore with another composition which, in turn, has the requisite specific binding capacity to the ligand to form a conjugate molecule. In the latter, the binding specificity of the conjugate is provided by the other compound and the light emitting capacity is provided by the fluorophore.

When a fluorophore is excited by a plane-polarized beam of light, the molecule will emit a polarized beam of light. The degree of polarization can be determined by the equation $$P = \frac{(IV - IH)}{(IV + IH)} \quad (1)$$

where: IV is the light intensity from the sample when excited by vertically polarized light and IH is the light intensity from the sample when excited by horizontally polarized light.

The degree of polarization can be used to determine the concentration of a particular analyte in a sample. For example, in an immunoassay, an analyte-fluorophore complex will have a low degree of polarization compared to a complex of a binding partner for the analyte, the analyte and the fluorophore. This is because the analyte-fluorophore complex, referred to herein as a "tracer," is smaller and thus has more random rotation in the time between its absorption of excitation light and the emission of fluorescence. Upon addition of the binding partner, however, the rotation of the bound-tracer is less random because of the greater mass of the compound. Thus, the degree of polarization for the bound tracer increases relative to that of the unbound tracer because the rotation of the bound tracer has decreased relative to the rotation of the unbound tracer. This inverse relationship between degree of polarization and rotation is the basis of fluorescence polarization immunoassay ("FPI") techniques.

FPI can be utilized to determine the concentration of an analyte in a sample containing or suspected of containing the analyte, such as, the concentration of an antigen, antibody, hapten, therapeutic drug or drug of abuse (or the metabolic products of a therapeutic drug or drug of abuse) in a bodily fluid. For example, if a drug of abuse is the analyte of interest to be measured, a known quantity of the drug is labeled with a fluorophore, such as fluorescein. The resultant drug-fluorescein complex is the tracer. The tracer and a specific binding partner for the drug can then be introduced into a patient sample suspected of including the drug. The tracer and any non-labelled drug in the sample will then compete for the limited number of binding sites on the specific binding partner. Each will have an equal probability of complexing with the specific binding partner. The observed polarization of fluorescence of the tracer becomes a value somewhere between that of the free and bound tracer. If the patient sample contains a high concentration of the drug, the observed polarization value will be low. This is because there is more of the drug in the sample than tracer and, as such, more of the drug from the sample will bind to the binding partner than will tracer. The tracer will remain relatively free in solution and, upon excitation by plane-polarized light, will maintain a relatively random rotation. However, if the patient sample contains a low concentration of the drug, the observed polarization value will be high because most of the tracer will be bound to the binding partner. Thus, the amount of the drug present in a sample is inversely proportional to the observed degree of polarization.

By sequentially exciting the reaction mixture of an immunoassay with vertically and then horizontally polarized light and analyzing only the vertical component of the emitted light, the polarization of fluorescence in the reaction container can be determined very accurately. The degree of polarization can be calculated from Equation 1, and the precise relationship between polarization and concentration of the unlabelled drug is established by measuring the polarization values of calibrators containing known concentrations of the drug. Alternatively, the reaction mixture of an immunoassay can be excited with vertically polarized light followed by analyzing, alternately, the horizontal and vertical component of the emitted light.

An inherent problem of FPI is light scattering. Light scattering may produce either an increase or a decrease in the apparent fluorescence signal. If the fluorescence value is artificially increased or decreased, then the concentration attributed to the analyte of interest will be similarly skewed. If the concentration of the analyte to be measured is necessary for diagnostic purposes, such skewed results can have severe and unacceptable consequences.

Previous light scattering correction methods involve addition of a buffer to a transparent container or cuvette, followed by addition of up to half of the test sample. A light sample intensity, or "scatter-correction" reading is then taken; this first reading is attributed to light scatter caused by the sample. Thereafter, a fluorophore is added to the sample, and after an appropriate incubation period, a second light intensity reading is taken. In order to determine a scatter corrected fluorescence reading due solely to the interaction of the fluorophore and analyte of interest, the scatter correction reading must be subtracted from the second light intensity reading. Thus, a primary disadvantage with this method is that it requires additional time to obtain the scatter-correction reading.

Because fluorescence is a valuable tool in the determination of the concentration of species of interest in a test sample, it would be useful to obtain a fluorescence value independent of light scattering.

SUMMARY OF THE INVENTION

The present invention corrects for light scattering by eliminating the fluorescence of a fluorophore with a fluorescence quenching material such that in the presence of such fluorescence quenching material, an emission value attributed to light scattering alone can be determined. Exemplary fluorescence quenching materials include pH altering substances, chemical compounds comprising the following constituents: —Cl, —Br, —I, —NHCOCH$_3$, —NO$_2$ and —COON, and the free ions of the foregoing constituents (e.g., I—, Cl—, etc.) As used herein, a "pH altering substance" is a substance which when added to the mixture of the sample and the fluorophore, lowers the pH of the mixture to about 4.0 or less. By adjusting the pH and obtaining both pre- and post-pH adjusted light emission values, a light scattering corrected emission light value can be derived.

In accordance with an embodiment of the disclosed method, a corrected emission light value for a sample to which a fluorophore has been added for the detection of an analyte in the sample can be determined by:
a) obtaining a first, uncorrected emission light value from the sample and fluorophore mixture;
b) adding at least one fluorescence quenching material to the mixture; and
c) obtaining a second, fluorophore-fluorescence-eliminated emission light value for the mixture.

A particularly preferred fluorescence quenching material is a pH altering substance. The pH altering substance, for example, eliminates, or "quenches," the fluorescence of the fluorophore. I.e., the emission light from step (a) is due to the fluorescence of the fluorophore and light scattering effects, while the emission light from step (c) is attributed principally to light scattering effects. Accordingly, by mathematically subtracting the second emission light value from the first emission light value, a "scatter-corrected" emission light value is derived.

For determination of the degree of polarization, the horizontal and vertical intensities from the sample (the sample being excited by horizontally and vertical polarized light) are each measured, at least one pH altering substance is added to the sample, and the resulting horizontal and vertical intensities from the resulting mixture (excited by horizontally and vertically polarized light) are each again measured. Thus, Equation 1 can be modified as follows:

$$P = \frac{(IV - IV_a) - (IH - IH_a)}{(IV - IV_a) + (IH - IH_a)}$$

where the IV and IH are as described, and IV$_a$ and IH$_a$ are the light intensity measurements from the sample-pH altering substance mixture when excited by vertically and horizontally polarized light.

DETAILED DESCRIPTION OF PREFERRED EMBODIMENTS

Fluorescence quenching substances can be effectively utilized to eliminate the fluorescence of a sample such that substantially the only remaining light is attributed to scattering effects. Exemplary fluorescence quenching substances include, but are not limited to: pH altering substances; compounds comprising the following constituents: —Cl, —Br, —I, —NHCOCH$_3$, —NO$_2$ and —COOH (with compounds comprising —I being particularly preferred); and free ions of the following (i.e., Chloride ions, Iodine ions, etc. with iodine ions being particularly preferred). Most preferred fluorescence quenching substances are pH altering substances.

A "pH altering substance" in accordance with the present invention is a substance which can lower the pH of the mixture of the fluorophore and the sample to a value at or below that at which the fluorophore will no longer fluoresce. For most fluorophores, this is a pH of about 4.0 or less. Examples of pH altering substances include inorganic and organic acids such as nitric acid, sulfuric acid, hydrobromic acid, phosphoric acid, hydrochloric acid, acetic acid, propionic acid, citric acid and succinic acid. Preferably, the pH altering substance is a strong acid, and most preferably the pH altering substance is hydrochloric acid.

The pH altering substance can be either in liquid or solid form. Liquid pH altering substances are preferred. Examples of solid pH altering substances include powdered succinic acid and citric acid.

Preferably, the molarity of the liquid pH altering substance is between about 0.1M and about 12.0M. As will be readily apparent by those skilled in the art, the molarity is principally dependent upon the relative strength (i.e. pH) of the acidic substance utilized, and the initial pH of the sample. For example, the concentration of a strong acid, such as hydrochloric acid, can have a molarity range of from about 0.1M to about 8.0M, whereas the concentration of a weak acid, such as acetic acid, can have a molarity range of from about 4.0M to about 12.0M. Preferably, a strong acidic substance is used because a minimal amount thereof can be added to the sample yet still achieve the desired quenching affect. Most preferably, 6.0M hydrochloric acid is utilized as the pH altering substance.

Virtually any fluorophore that is pH dependent can be utilized; pH dependency is necessary in order to ensure that as the pH of the sample changes with the addition of the pH altering substance, the behavior of the fluorophore will similarly change. Examples of such fluorophores include fluorescein, the salts of fluorescein, rhodamine and the derivatives of rhodamine, such as TEXAS RED TM (Molecular Probes, Eugene, Oreg.). Sodium fluorescein is a particularly useful fluorophore. As noted, fluorescence of a fluorophore is typically measured at the pH of its maximum fluorescence intensity; thus, the pH of the sample prior to addition of the pH altering substance depends on the particular fluorophore being used. Most fluorophores have their maximum fluorescence in the weakly acid-to-alkaline side of the pH spectrum. The pH of the sample will thus typically be in the range of from about 6 to about 9 prior to addition of the pH altering substance.

Because the quantum yield of fluorescence decreases as the temperature of the test sample increases (due to increased collisional deactivation of the excited molecules), the temperature of the test sample should remain relatively constant i.e., within about ±1° of a set temperature point. Preferably the temperature of the test sample is maintained between about 20° C. and about 40° C.

Typically, the test sample, for example a bodily fluid such as whole blood, serum, plasma, urine or cerebro spinal fluid, is diluted prior to analysis. Such dilution minimizes the interference by the sample with the analysis thereof caused by altering the transmission of light through the sample medium. Accordingly, the sample:diluent ratio should be at least about 1 part sample to about 20 parts diluent (1:20), preferably between about 1:40 and about 1:200, and most preferably about 1:100. Preferably, the diluent is a buffered solution. A phosphate buffered saline solution is particularly useful because its buffer strength is sufficiently weak that only a minimal amount of a pH altering substance is needed to lower the pH of the diluted sample to the desired level of about 4.0 or less. Such diluents are well known; a particularly useful phosphate buffered saline diluent is ICS TM Diluent (Beckman Instruments, Inc., Brea, Calif.).

Although not limited thereto, the present invention is applicable to competitive and "sandwich" fluorescence assays. Competitive fluorescence assays usually comprise the following components: 1) a predetermined amount of the analyte of interest or an "analog" thereof, i.e. a compound capable of competing with the analyte of interest in the sample for binding sites on the specific binding partner to the analyte. The analyte or analog is labelled with a fluorophore. This component is referred to as the "analyte-fluorophore tracer"; 2) a specific binding partner to the analyte on the tracer; 3) a sample which may contain the analyte of interest. These three components are then added to a cuvette for subsequent analysis. The analyte-fluorophore tracer and any analyte in the sample compete for binding sites on the specific binding partner. After a sufficient incubation period, the sample is irradiated with light in the absorption band of the fluorophore and a first, uncorrected intensity of the emission from the sample is determined at at least one wavelength.

Sandwich fluorescence assays usually comprise the following components: 1) a quantity of an insolubilized first specific binding partner to the analyte of interest or an analog thereof; 2) a known quantity of a soluble, second specific binding partner to the analyte or analog, the soluble, second specific binding partner being labelled with a fluorophore; 3) a sample which may contain the analyte of interest. These three components are then mixed, and after a sufficient incubation period, insoluble, ternary complexes comprising insolubilized first specific binding partner, sample analyte and soluble, labeled second binding partner will be formed. Unreacted insolubilized first binding partner and any ternary complexes formed are then separated from the remaining sample. This is followed by irradiating the remaining sample with light in the adsorption band of the fluorophore and an uncorrected intensity of the emission from the sample is determined at least one wavelength. Because there is a known amount of soluble, labeled second specific binding partner added to the mixture, a sample containing a high concentration of the analyte will lead to the formation of many insolubilized ternary complexes such that the remaining sample will contain little soluble, labeled second specific binding partner. Alternatively, when the concentration of sample analyte is low, ternary complex formation will be low such that the separated sample will contain most of the soluble, labelled second binding partner. Therefore, for sandwich fluorescence assays, the concentration of sample analyte is inversely proportional to the amount of detected fluorophore. An insolubilized fluorophore can be detected using the foregoing protocol, or after subsequent release following separation of the insolubilized fluorophore from materials not insolubilized.

For both the competitive and sandwich fluorescence assays, a pH altering substance is added to the sample and the sample is again irradiated with light in the absorption band of the fluorophore. A pH altered light emission value from the sample at at least one wavelength is then determined.

When the pH altering substance is a liquid, its addition to the cuvette will increase the volume in the cuvette. This will have the affect of creating a "volume dilution" effect on the pH altered intensity value. In order to correct for the volume dilution effect, it is necessary to increase this intensity value upwards by mathematically multiplying the pH altered intensity value by the quotient derived from dividing the total of the liquid volume of the cuvette after addition of the pH altering substance, by the total of the liquid volume of the cuvette prior to addition of the substance. A nonliquid pH altering substance will typically not create a volume dilution effect because the amount added to the sample will typically not increase the volume of the sample. When, however, the amount of a non-liquid pH altering substance added to the sample increases the volume of the sample, the intensity value is increased upwards as described above.

The pH altered light emission value is the value attributed to light scattering; thus, this value is subtracted from the initial (uncorrected) light emission value in order to obtain a scatter-corrected light emission value. The corrected emission value can then be compared to corrected emission values for standards containing known amounts of the analyte of interest.

EXAMPLES

The following Examples are presented for illustration purposes only and are not intended to limit the scope of the invention, this disclosure, or the claims that follow.

EXAMPLE I

Fluorescence values were obtained from a Perkin-Elmer Fluorescence Spectrophotometer 650-40, set at high gain, with the excitation wavelength set at 460 nm (slit width: 5 nm) and the emission wavelength set at 515 nm (slit width: 10 nm). Light intensity readings were taken of a cuvette containing: (1) 2 ml of ICS TM diluent (Beckman Instruments, Inc., Brea, Calif., Lot No. L908078); (2) 20 µl of water; (3) 20 µl of 10.6M sodium fluorescein (Mallincrodt); and (4) 100 μl of 6M HCl. Water was used as the sample because water is essentially "scatter free". Separate readings were taken after the addition of each of the four constituents. The values obtained, including mean values, are set forth in Table I:

TABLE I

| Constituent | Scatter Free Sample Reading | | | | | |
|---|---|---|---|---|---|---|
| | 1 | 2 | 3 | 4 | 5 | Mean |
| diluent | 0 | 0 | 0 | 0 | 0 | 0 |
| water | 1.5 | 6.8 | 1.2 | 0.3 | 0.6 | 2.1 |
| sodium fluorescein | 122.0 | 115.0 | 96.4 | 100.01 | 99.1 | 106.5 |
| HCl | 2.1 | 2.2 | 1.5 | 1.8 | 2.1 | 1.9 |

As the data from Table I demonstrates, addition of a pH altering substance to the sample has the affect of quenching the reading attributed to the addition of the fluorophore. I.e., even though the fluorophore is still present in the cuvette, the pH altering substance eliminated its fluorescence. Stated again, because water and the diluent are essentially scatter-free, any fluorescence reading obtained from such a sample alone should be attributed to factors other than the sample (the cuvette, etc.). Therefore, addition of a pH altering substance to a sample container including such a scatter-free solution and a fluorophore should lower the fluorescence reading to that of the scatter free solution alone.

The volume of the cuvette after addition of 6M HCL was 2.14 ml, and the volume prior to acid addition was 2.04 ml. Accordingly, when the mean fluorophore reading obtained after addition of the acid is corrected upwards due to the volume dilution effect:

$$1.9*(2.14/2.04)=2.0$$

then the volume corrected reading is approximately the same as the reading for the scatter-free solution (water plus diluent) alone (2.1). As used herein, the symbol "*" indicates a mathematical multiplication symbol and the symbol "/" indicates a mathematical division symbol.

Example I therefore verifies that a pH altering substance can be utilized to obtain a corrected fluorescence by eliminating the fluorescence attributed to the fluorophore.

EXAMPLE II

A second set of readings was obtained using the protocol of Example I with the exception that 20 μl of serum (gentamycin sample, SmithKline Biosciences Laboratory) was utilized instead of water. Serum, unlike water, is not scatter-free. Readings obtained are set forth in Table II:

TABLE II

| Constituent | 20 μl Gentamycin Serum Sample Reading | | | | | |
|---|---|---|---|---|---|---|
| | 1 | 2 | 3 | 4 | 5 | Mean |
| diluent | 0 | 0 | 0 | 0 | 0 | |
| serum | 11.1 | 12.0 | 18.7 | 22.8 | 12.6 | 15.4 |
| sodium fluorescein | 97.4 | 100.0 | 106.0 | 117.0 | 102.1 | 104.5 |
| HCl | 10.8 | 10.8 | 11.1 | 11.5 | 10.4 | 10.9 |

The mean value of 15.4 for serum is attributed to light scattering; however, addition of a pH altering substance permits observation of the scatter portion of the signal even when the fluorophore is present. The post-pH altering substance addition mean reading, volume-dilution corrected, is calculated as follows:

$$10.9*(2.14/2.04)=11.2$$

Thus, rather than requiring the use of a portion of the sample and diluent to obtain the scatter-correction reading, the results of Example II demonstrate that the scatter-correction reading can be taken as the final step, i.e. after the analysis of the sample has been completed. As demonstrated, this is due to the ability of the pH altering substance to quench the fluorescence of the fluorophore.

EXAMPLE III

The protocol of Example II was repeated, with exception that instead of utilizing 20 μl of the aforementioned serum sample, a 50 μl sample was tested. Readings obtained are set forth in Table III:

TABLE III

| Constituent | 50 μl Gentamycin Serum Sample Reading | | | | | |
|---|---|---|---|---|---|---|
| | 1 | 2 | 3 | 4 | 5 | Mean |
| diluent | .2 | .2 | .05 | .05 | 0.0 | 0.1 |
| serum | 15.8 | 16.4 | 15.6 | 19.4 | 15.7 | 16.6 |
| sodium fluorescein | 87.4 | 95.5 | 91.0 | 108.0 | 95.2 | 95.4 |
| HCl | 14.9 | 15.0 | 15.4 | 12.4 | 14.5 | 14.4 |

As with the results of Example II, the results of Example III demonstrate that the scatter-correction reading can be taken after addition of a fluorophore to a sample when a pH altering substance has been added to the sample including that fluorophore. For Example III, the volume dilution corrected reading attributed to light scattering is calculated as follows, with subtraction of the reading attributed to the diluent incorporated into the formulation:

$$(14.4-0.1)*(2.17/2.07)=15.0$$

Examples I to III demonstrate that the problems associated with previous scatter correction methodologies are avoided. When the disclosed methodology is utilized, the inconveniences of: a) obtaining a light scatter value from a portion of the sample; b) storing the data for that cuvette; c) adding a tracer to the cuvette and waiting for a period of time sufficient for incubation; d) obtaining a second measurement (fluorescence plus scatter); and e) subtracting the scatter value from the second measurement, are nullified. Utilization of the present method negates the pre-measurement and the delay associated with incubation. The invention readily lends itself to application to instruments that are currently utilized for the types of analyses discussed herein.

The above examples are of preferred embodiments of the disclosed invention. Modifications of the methods described that are within the purview of those in the art are intended to be within the scope of the invention. For example, it is considered to be within the purview of those skilled in the art to determine different volume amounts for different pH altering liquid substances, as well as specific amounts of non-liquid pH altering substance that may be utilized to achieve the objectives of the disclosed invention.

What is claimed is:

1. A method for determining a corrected emission light value for a sample comprising an extrinsic fluorophore, said fluorophore having a dependent fluorescence and being bound to a chemical entity capable of reacting in a specific binding reaction, said method comprising the following steps:

a) obtaining a first emission light value by irradiating the sample and the fluorophore with excitation light in the absorption band of said fluorophore and detecting emission light, b) adding an amount of a pH altering substance to said sample, said amount of pH altering substance being sufficient to alter the pH of the sample to a value sufficiently low to quench the fluorescence, c) obtaining a second emission light value by irradiating the sample, the fluorophore and the pH altering substance with excitation light in the absorption band of said fluorophore and detecting emission light, and d) subtracting the value obtained from step (c) from the value obtained from step (a), wherein the result of step (d) is an the corrected emission light value for said sample.

2. The method of claim 1 wherein the pH altering substance is selected form the group consisting of nitric acid, sulfuric acid, hydrobromic acid, phosphoric acid, hydrochloric acid, acetic acid, propionic acid, citric acid and succinic acid.

3. The method of claim 1 wherein the fluorescence quenching substance is hydrochloric acid.

4. The method of claim 1 wherein the molarity of the pH altering substance is between about 0.1 and about 12.0.

5. The method of claim 1 wherein the molarity of the pH altering substance is between about 0.1 and about 8.0.

6. The method of claim 1 wherein the fluorescence quenching substance is hydrochloric acid having a molarity of about 6.0.

7. The method of claim 1 wherein the fluorophore is selected from the group consisting of rhodamine, rhodamine derivatives, fluorescein and salts of fluorescein.

8. The method of claim 1 wherein the fluorophore is sodium fluorescein.

9. The method of claim 1 wherein the pH altering substance is in a non-liquid form.

10. The method of claim 1 wherein the pH altering substance is in a liquid form.

11. The method of claim 10 including the additional step of multiplying the second emission value with the quotient resulting from mathematically dividing the volume of sample plus the volume of the liquid pH altering substance, by the volume of the sample.

12. A method for determining the amount of analyte in a sample, said method based upon an emission light value of the sample comprising the steps of:

a) combining in an aqueous medium: (1) the sample; (2) an analyte-fluorophore complex wherein said fluorophore has a pH dependent fluorescence and wherein the binding of a binding partner to said analyte reduces the emission intensity of said complex; and (3) a binding partner to said analyte, said combining being under conditions for binding said binding partner to said analyte, b) obtaining a first emission light value by irradiating said medium with light in the absorption band of said fluorophore and detecting emission light, c) adding an amount of a pH altering substance to said medium, said amount of pH altering substance being sufficient to alter the pH of the medium to a value sufficiently low to quench the fluorescence,, d) obtaining a second emission light value by irradiating said medium with light in the absorption band of said fluorophore and detecting emission light, and e) subtracting the value obtained from step (d) by the value obtained from step b), wherein the result of step (e) is compared with emission light values of known amounts of the analyte to determine the amount of analyte in the sample.

13. The method of claim 12 wherein said pH altering substance is an acid.

14. The method of claim 12 wherein the pH altering substance is in a non-liquid form.

15. The method of claim 12 wherein the pH altering substance is in a liquid form.

16. The method of claim 12 wherein the pH altering substance is selected form the group consisting of nitric acid, sulfuric acid, hydrobromic acid, phosphoric acid, hydrochloric acid, acetic acid, propionic acid, citric acid, and succinic acid.

17. The method of claim 15 including the additional step of multiplying the second emission light value with the quotient resulting from mathematically dividing the volume of medium plus the volume of the pH altering substance by the volume of the medium.

18. The method of claim 12 wherein the pH altering substance is hydrochloric acid.

19. The method of claim 12 wherein the pH altering substance is hydrochloric acid having a molarity of about 6.0.

20. The method of claim 12 wherein the molarity of the pH altering substance is between about 0.1 and about 12.0.

21. The method of claim 12 wherein the molarity of the pH altering substance is between about 0.1 and about 8.0.

22. The method of claim 12 wherein the fluorophore is selected from the group consisting of rhodamine, rhodamine derivatives, fluorescein and salts of fluorescein.

23. The method of claim 12 wherein the fluorophore is sodium fluorescein.

24. A method for determining the amount of analyte in a sample based upon an emission light value of the sample comprising the steps of:

a) combining in an aqueous medium: (1) the sample; (2) a first, insolubilized binding partner to said analyte; and (3) a second, soluble binding partner to said analyte labelled with a fluorophore, under conditions which allow for said insolubilized binding partner and said soluble binding partner to bind to analyte present in said sample, said fluorophore having a pH dependent fluorescence, b) separating substantially all insolubilized material from non-insolubilized material of said medium, c) obtaining a first emission light value by irradiating said medium with light in the absorption band of said fluorophore and detecting emission light, d) adding an amount of a pH altering substance to said medium, said amount of pH altering substance being sufficient to alter the pH of the medium to a value sufficiently low to quench the fluorescence, e) obtaining a second emission light value by irradiating said medium with light in the absorption band of said fluorophore and detecting emission light, and f) subtracting the value obtained from step e) by the value obtained from step c), wherein the result of step f) is compared with emission light value of known amounts of the analyte to determine the amount of analyte in the sample.

25. The method of claim 24 wherein said pH altering substance is an acid.

26. The method of claim 24 wherein the pH altering substance is in a non-liquid form.

27. The method of claim 24 wherein the pH altering substance is in a liquid form.

28. The method of claim 24 wherein the pH altering substance is selected form the group consisting of nitric acid, sulfuric acid, hydrobromic acid, phosphoric acid, hydrochloric acid, acetic acid, propionic acid, citric acid, and succinic acid.

29. The method of claim 27 including the additional step of multiplying the second emission light value with the quotient resulting from mathematically dividing the volume of medium plus the volume of said pH altering substance by the volume of the medium.

30. The method of claim 24 wherein the pH altering substance is hydrochloric acid.

31. The method of claim 24 wherein the pH altering substance is hydrochloric acid having a molarity of about 6.0.

32. The method of claim 24 wherein the molarity of the pH altering substance is between about 0.1 and about 12.0.

33. The method of claim 24 wherein the molarity of the pH altering substance is between about 0.1 and about 8.0.

34. The method of claim 24 wherein the fluorophore is selected from the group consisting of rhodamine, rhodamine derivatives, fluorescein and salts of fluorescein.

35. The method of claim 24 wherein the fluorophore is sodium fluorescein.

36. A method of determining a corrected degree of polarization of a sample comprising a pH dependent fluorophore irradiated with both horizontally and vertically polarized light, said fluorophore having a pH dependent fluorescence and being bound to a chemical entity capable of reacting in a specific binding reaction, said method comprising the steps of a) obtaining an emission light value, IV, by irradiating the sample with vertically polarized light in the adsorption band of said fluorophore and detecting emission light;

b) obtaining an emission light value, IH, by irradiating the sample with horizontally polarized light in the adsorption band of said fluorophore and detecting emission light;

c) adding an amount of a pH altering substance to said sample said amount of pH altering substance being sufficient to alter the pH of the medium to a value sufficiently low to quench the fluorescence;

d) obtaining an emission light value, $IV_a$, by irradiating the sample with vertically polarized light in the adsorption band of said fluorophore and detecting emission light; and e) obtaining an emission light value $IH_a$, by irradiating the sample with horizontally polarized light in the adsorption band of said fluorophore and detecting emission light; and f) subjecting the values IV, IH, $IV_a$, and $IH_a$ to the following transformation $$\frac{(IV - IV_a) - (IH - IH_a)}{(IV - IV_a) + (IH - IH_a)}$$

wherein the resulting value is the corrected degree of polarization for said sample.

* * * * *